(12) United States Patent
Park et al.

(10) Patent No.: US 8,862,205 B2
(45) Date of Patent: Oct. 14, 2014

(54) THERAPEUTIC MICROROBOT SYSTEM FOR BRAIN AND SPINAL CORD DISEASES

(75) Inventors: Suk Ho Park, Gwangju (KR); Jong Oh Park, Gyeonggi-do (KR); Kyoung Rae Cha, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 97 days.

(21) Appl. No.: 13/696,720

(22) PCT Filed: Apr. 5, 2012

(86) PCT No.: PCT/KR2012/002572
§ 371 (c)(1),
(2), (4) Date: Nov. 7, 2012

(87) PCT Pub. No.: WO2012/138144
PCT Pub. Date: Oct. 11, 2012

(65) Prior Publication Data
US 2013/0060130 A1 Mar. 7, 2013

(30) Foreign Application Priority Data
Apr. 5, 2011 (KR) .................. 10-2011-0031270

(51) Int. Cl.
*A61B 6/00* (2006.01)
*A61B 19/00* (2006.01)
*A61B 6/12* (2006.01)
*A61B 6/03* (2006.01)

(52) U.S. Cl.
CPC .............. *A61B 6/12* (2013.01); *A61B 19/2203* (2013.01); *A61B 6/481* (2013.01); *A61B 6/504* (2013.01); *A61B 2019/2249* (2013.01); *A61B 2019/5238* (2013.01); *A61B 6/466* (2013.01); *A61B 2019/2253* (2013.01); *A61B 19/50* (2013.01); *A61B 19/22* (2013.01); *A61B 6/037* (2013.01)
USPC .......................................... 600/424; 600/427

(58) Field of Classification Search
USPC ........... 600/407, 411, 424, 425, 427; 335/229
See application file for complete search history.

(56) References Cited

U.S. PATENT DOCUMENTS 7,596,403 B2 9/2009 Horn
7,643,865 B2 1/2010 Iddan et al.
(Continued)

FOREIGN PATENT DOCUMENTS

KR 10-0457752 B1 12/2004
KR 10-0615881 B1 8/2006
KR 10-2010-0048728 A 5/2010

OTHER PUBLICATIONS

William Anderst et al., "Validation of Three-Dimensional Model-Based Tibio-Femoral Tracking During Running", Med Eng Phys., Jan. 2009, pp. 10-16, vol. 31, No. 1.
(Continued)

*Primary Examiner* — Michael Rozanski
(74) *Attorney, Agent, or Firm* — Rabin & Berdo, P.C.

(57) ABSTRACT

Disclosed is a microrobot for the therapy of brain/spinal cord diseases. It comprises a microrobot comprising a driving unit having a magnet therein, and a therapeutic means or drug delivery means for treating a disease lesion; a microrobot driving module for performing and controlling various motions of the microrobot by generating an electromagnetic force through an electromagnetic coil system; an imaging module for imaging a thecal sac filled with cerebrospinal fluid, a ventricle, and the microrobot; a diagnosis module for diagnosing the brain/spinal cord disease, based on a pre-operative image produced by the imaging module; and a navigation module for planning a moving path for the microrobot, based on the pre-operative image produced by the imaging module and for monitoring the microrobot through an intraoperative image produced by the imaging module.

9 Claims, 12 Drawing Sheets

(56) References Cited

U.S. PATENT DOCUMENTS

| | | |
|---|---|---|
| 7,865,229 B2 | 1/2011 | Horn |
| 2006/0004276 A1 | 1/2006 | Iddan et al. |
| 2006/0036166 A1 | 2/2006 | Horn |
| 2008/0300458 A1 | 12/2008 | Kim et al. |
| 2009/0036902 A1 | 2/2009 | DiMaio et al. |
| 2009/0292182 A1 | 11/2009 | Horn |
| 2011/0184388 A1 | 7/2011 | Park et al. |

OTHER PUBLICATIONS

Semi Jeong et al., "Novel electromagnetic actuation (EMA) method for 3-dimensional locomotion of intravascular microrobot", Sensors and Actuators A, 2010, pp. 118-125, vol. 157.

Hyunchul Choi et al., "EMA system with gradient and uniform saddle coils for 3D locomotion of microrobot", Sensors and Actuators A, 2010, pp. 410-417, vol. 163.

THERAPEUTIC MICROROBOT SYSTEM FOR BRAIN AND SPINAL CORD DISEASES

TECHNICAL FIELD

The present invention relates, in general, to a therapeutic microrobot system and, more particularly, to a therapeutic microrobot system for brain and spinal cord diseases.

BACKGROUND ART

In a surgical operation for the therapy of brain or spinal cord diseases, typically, a hard tubular device is used for access to an intrathecal or intraventricular lesion (e.g., ependyma, thrombus, tumor, etc) which is then perforated or removed with the aid of a subminiature manipulator. For example, cerebrospinal fluid produced in the cerebral ventricle flows in the spinal direction through very narrow tubes. When even a part of the circulation path of the cerebrospinal fluid is closed, it is accumulated in the cranial cavity or the spinal cavity, causing increased intracranial pressure, with the concomitant generation of a headache and emesis. In a severe case, a brain developmental disorder, called hydrocephalus, is generated. Representative among common surgeries for the treatment of hydrocephalus are a shunt operation and endoscopic third ventriculostomy.

The insertion of a shunt into the cerebral ventricle diverts fluid from the brain into the abdominal or thoracic cavity where it is safely absorbed into the blood stream. The shunt conduit may be provided with a valve by which the amount of the cerebrospinal fluid can be regulated depending on the cranial pressure. In former days, in order to change the pressure, the valve itself had to be replaced with a new one by re-operation. Recently, valves that can regulate the pressure ex vivo have been developed, allowing the pressure to be readily reset depending on the condition of the patient. Shunt therapy is the most common surgery for the treatment of hydrocephalus, and can be applied to both communicating and non-communicating hydrocephalus.

Endoscopic third ventriculostomy is a surgical procedure that has more recently been developed, and in which an opening is created in the floor of the third ventricle using an endoscope upon the enlargement of the ventricle in non-communicating hydrocephalus, allowing communication between the ventricle and the subarachnoid space. Endoscopic third ventriculostomy has the advantage of the natural circulation of cerebrospinal fluid without the implantation of a foreign object, such as a shunt, but is used only to treat non-communicating hydrocephalus. In addition, endoscopic third ventriculostomy requires that the ventricle has a sufficient size and the floor of the third ventricle and its surrounding blood vessels be suitably structured to perform the operation. Further, the probability of success is high only when the operation is performed on children one or more years old. It is also known that endoscopic third ventriculostomy does not work well on hydrocephalus caused by cerebral hemorrhage or central nervous system infection because the superior sagittal sinus where the cerebral spinal fluid is finally absorbed is often obstructed. Unless hydrocephalus is improved with endoscopic third ventriculostomy, an additional shunt therapy should be undertaken.

DISCLOSURE OF INVENTION

Technical Problem

Brain surgery including a shunt operation is very invasive because a hole is created on the skull to treat the cerebra. Such an invasive operation procedure may cause serious problems such as infections or unexpectable side effects.

Accordingly, the present invention has been made keeping in mind the above problems occurring in the prior art, and an object of the present invention is to provide a microrobot system applicable to the treatment of brain and spinal cord diseases.

It should be noted that this object is illustrative, and is not set to limit the scope of the present invention.

Solution to Problem

In accordance with an aspect thereof, the present invention provides a microrobot driving system, comprising: a microrobot driving module, equipped with an electromagnetic coil system, for performing and controlling various motions of a microrobot by generating an electromagnetic force through the electromagnetic coil system;

a brain/spinal cord imaging module for imaging a thecal sac filled with cerebrospinal fluid, a ventricle, and the microrobot;

a diagnosis module for diagnosing the brain/spinal cord disease, based on a pre-operative image produced by the brain/spinal cord imaging module; and a navigation module for planning a moving path for the microrobot, based on the pre-operative image produced by the imaging module and for monitoring the microrobot through an intraoperative image produced by the imaging module.

In accordance with another aspect thereof, the present invention provides a microrobot system for the therapy of a brain/spinal cord disease, comprising:

a microrobot comprising a driving unit having a magnet therein, and a therapeutic means and/or drug delivery means for treating a disease lesion;

a microrobot driving module for performing and controlling various motions of the microrobot by generating an electromagnetic force through an electromagnetic coil system, said electromagnetic force acting as a driving force on the magnet;

a brain/spinal cord imaging module for imaging a thecal sac filled with cerebrospinal fluid, a ventricle, and the microrobot;

a diagnosis module for diagnosing the brain/spinal cord disease, based on a pre-operative image produced by the brain/spinal cord imaging module; and a navigation module for planning a moving path for the microrobot, based on the pre-operative image produced by the imaging module and for monitoring the microrobot through an intraoperative image produced by the imaging module.

In one embodiment, the microrobot driving module comprises the electromagnetic coil system, a power supply for supplying electric power to the coil system, and an electric power controlling system.

In another embodiment, the brain/spinal cord imaging module is a bi-plane X-ray angiographic device capable of producing three-dimensional cerebrospinal images.

In a further embodiment, the diagnosis module comprises: a comparison means for comparing an image produced by the bi-plane X-ray angiographic device with clinical data; a determination means for determining the presence and severity of a disease; and a display means for displaying the determination result obtained by the determination means. The clinical data may be installed within the diagnosis module or provided from an external source.

In still a further embodiment, the navigation module comprises: a design means for planning a moving path of the microrobot with reference to the three-dimensional pre-operative image produced by the brain/spinal cord imaging module; and a microrobot indicating means for indicating the practical position of the microrobot using pre- and intra-operative images produced by the imaging module.

In still another embodiment, the therapeutic means may be a puncher or micro-scissors.

In accordance with a further aspect thereof, the present invention provides a method for treating a brain/spinal cord disease using a microrobot, comprising:

extracting and processing a three-dimensional pre-operative cerebrospinal image using a bi-plane X-ray angiographic device;

planning a moving path of the microrobot from the three-dimensional pre-operative cerebrospinal image using a navigation module;

introducing the microrobot into a thecal sac of a patient, said microrobot being equipped with a driving unit having a magnet therein, and a therapeutic means or a drug delivery means;

detecting positions of a ventricle, the thecal sac and the microrobot with the bi-plane X-ray angiographic device and the navigation module by photographing intra-operative cerebrospinal images;

moving the microrobot along the planned moving path using a microrobot driving module equipped with an electromagnetic coil system;

allowing the microrobot to reach a lesion, followed by performing a medical treatment for a lesion using the therapeutic means or the drug delivery means; and extracting the microrobot counter to the moving path under control of the microrobot driving module to exclude the microrobot from the body.

In one embodiment of this aspect, the navigation module comprises: a design means for planning a moving path of the microrobot with reference to the three-dimensional pre-operative cerebrospinal image extracted and processed by the brain/spinal cord imaging module; and a microrobot indicating means for indicating a practical position of the microrobot using three-dimensional pre- and intra-operative images.

In another embodiment, the microrobot driving module comprises an electromagnetic coil system, a power supply for supplying an electric power to the coil system, and an electric power controlling system.

In a further embodiment, the microrobot is introduced into the thecal sac using a syringe needle or a catheter.

In a still further embodiment, the therapeutic means is a puncher for perforating an obstruction or micro-scissors for dissecting an obstruction, said obstruction including an ependyma.

Advantageous Effects of Invention

In addition to being useful for the therapy of various cerebrospinal diseases, as described hitherto, the microrobot system in accordance with the present invention guarantees a minimally invasive surgery method which has an advantage over conventional methods in which invasive needle-type devices are used to punch the ependyma or to deliver a drug. It should be noted that the scope of the present invention is not limited to these effects.

BRIEF DESCRIPTION OF DRAWINGS

The above and other objects, features and other advantages of the present invention will be more clearly understood from the following detailed description taken in conjunction with the accompanying drawings, in which.

BRIEF DESCRIPTION OF REFERENCE NUMERALS

Figure 1:
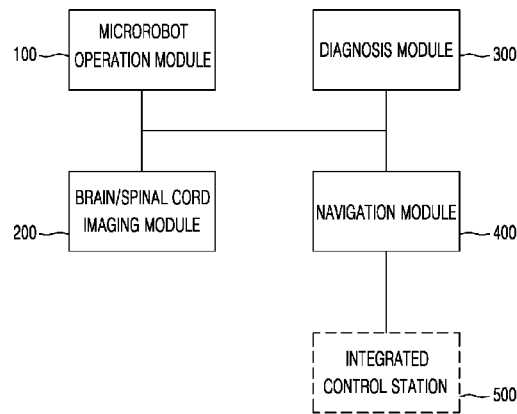
FIG. 1 is a schematic diagram illustrating a microrobot driving system for the therapy of brain/spinal cord diseases in accordance with an embodiment of the present invention.

1: microrobot operation system for the therapy of brain/spinal cord diseases
10: brain/spinal cord imaging and microrobot operation unit
20: integrated control unit 30: patient
40: bed 100: microrobot operation module
110: coil system
200: brain/spinal cord imaging module
210: bi-plane X-ray angiographic device
211: radio-active ray source
212: image sensor 300: diagnosis module
310: clinical database 320: comparison means
330: determination means 340: display means
400: navigation module 410: expected moving path
420: syringe needle 430: thecal sac
440: real moving path 450: lesion
500: integrated control station 600: microrobot
610: driving unit 620: therapeutic means
630: ependyma 640: punched or dissected region
650: drug

BEST MODE FOR CARRYING OUT THE INVENTION

Reference should now be made to the drawings, in which the same reference numerals are used throughout to designate the same or similar components.

FIG. 1 shows a schematic view that illustrates a microrobot driving system 1 for the therapy of brain/spinal cord diseases in accordance with an embodiment of the present invention.

Figure 2:
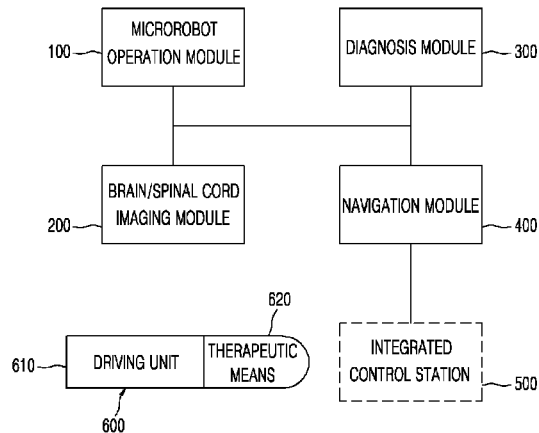
FIG. 2 is a schematic diagram illustrating a microrobot system for the therapy of brain/spinal cord diseases.

As shown in FIG. 1, the microrobot driving system 1 for the therapy of brain/spinal cord diseases in accordance with an embodiment of the present invention comprises a microrobot driving module 100, a brain/spinal cord imaging module 200, a diagnosis module 300, and a navigation module 400. Optionally, each of the diagnosis module 300 and the navigation module 400 may be provided as software. Separately, the microrobot driving system may further comprise an integrated control station 500 (represented by dotted lines in FIG. 1). According to another embodiment of the present invention, as shown in FIG. 2, the microrobot driving system 1 for the therapy of brain/spinal cord diseases is combined with a locomotive therapeutic microrobot 600 to complete a therapeutic microrobot system 2 for brain and spinal cord diseases. The integrated control station 500 may consist of computer hardware comprising an input/output bus, a display device, a central process unit, an input device, a main memory unit, and other devices, and comprehensive software installed in the main memory unit of the computer hardware, which, together with the diagnosis module 300 and the navigation module 400, allows the microrobot driving system to be synthetically operated. Alternatively, the comprehensive software may not be installed in the main memory unit of the hardware, but may be separately provided in an installable form in an auxiliary memory unit such as an MD, CD-ROM, DVD-ROM, USB memory, etc. The input device may be a keyboard and/or a pointing device, such as a mouse, a trackball, a joystick, or a touchpad. The display device may be a monitor such as a CRT monitor, an LCD monitor, or a PDP monitor. It may be provided with a touch panel and display three-dimensional images.

Figure 3:
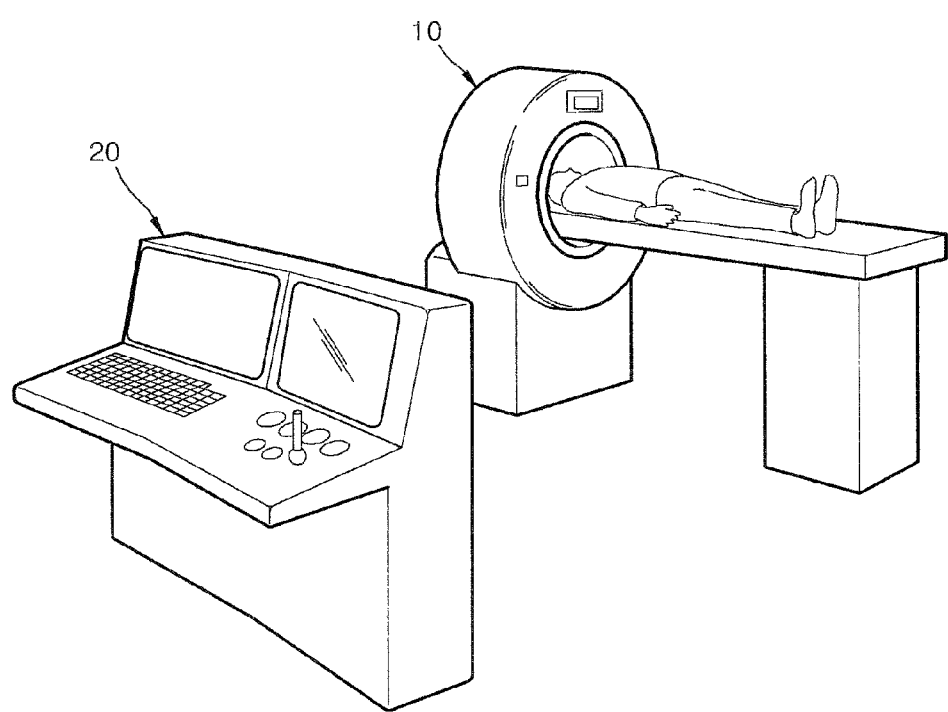
FIG. 3 is a schematic perspective view illustrating a microrobot driving system for the therapy of brain/spinal cord diseases in accordance with an embodiment of the present invention.

Referring to FIG. 3, the microrobot driving system 1 in accordance with an embodiment of the present invention is schematically illustrated. As seen in FIG. 3, the microrobot driving module 100 and the brain/spinal cord imaging module 200 may be installed in one housing to form a brain/spinal cord imaging/microrobot driving unit 10 in order for the microrobot driving system of the present invention to be adapted to perform an intraoperative imaging process. That is, the therapeutic microrobot system could image the brain/spinal cord as well as move the microrobot displayed in real time on the monitor along a given path, simultaneously. Accordingly, the brain/spinal cord to be imaged and the microrobot to be moved within the brain/spinal cord may occupy the same position.

In addition, as seen in FIG. 3, the diagnosis module 300 and the navigation module 400 function to diagnose a specific disease or establish or display a moving path for the microrobot, and are incorporated into an integrated control station or unit (20), a computer system.

Below, a detailed description will be given of each of the constitutional elements constituting the microrobot driving system of the present invention.

Figure 4:
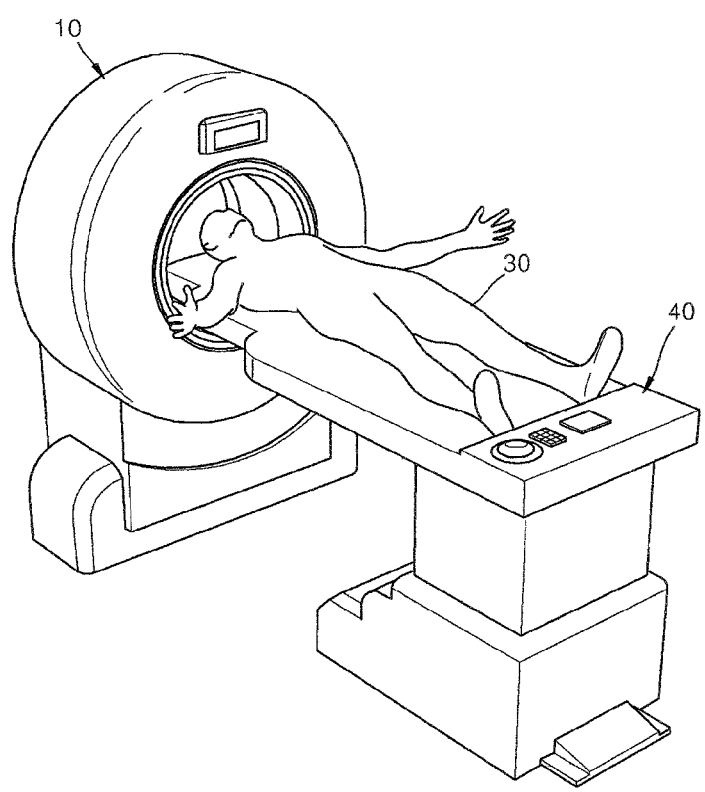
FIG. 4 is a schematic view illustrating a brain/spinal imaging and microrobot driving unit of the microrobot driving system for the therapy of brain/spinal cord diseases in accordance with an embodiment of the present invention.

Turning to FIG. 4, a bran/spinal cord imaging and microrobot driving unit 10 is constructed by integrating the microrobot driving module 100 and the bran/spinal cord imaging module 200 into one housing. According to one embodiment of the present invention, the brain/spinal cord imaging and microrobot driving unit 10 may have a donut- or hemisphere structure such that the upper body of a patient 30 goes in and out the hole of the structure. While lying down on an immobilized bed 40, the patient 30 may be diagnosed or treated. Alternatively, the patient 30 may lie on a mobile bed 40 so that the upper body is allowed to go through the brain/spinal cord imaging and microrobot driving unit 10.

Figure 5:
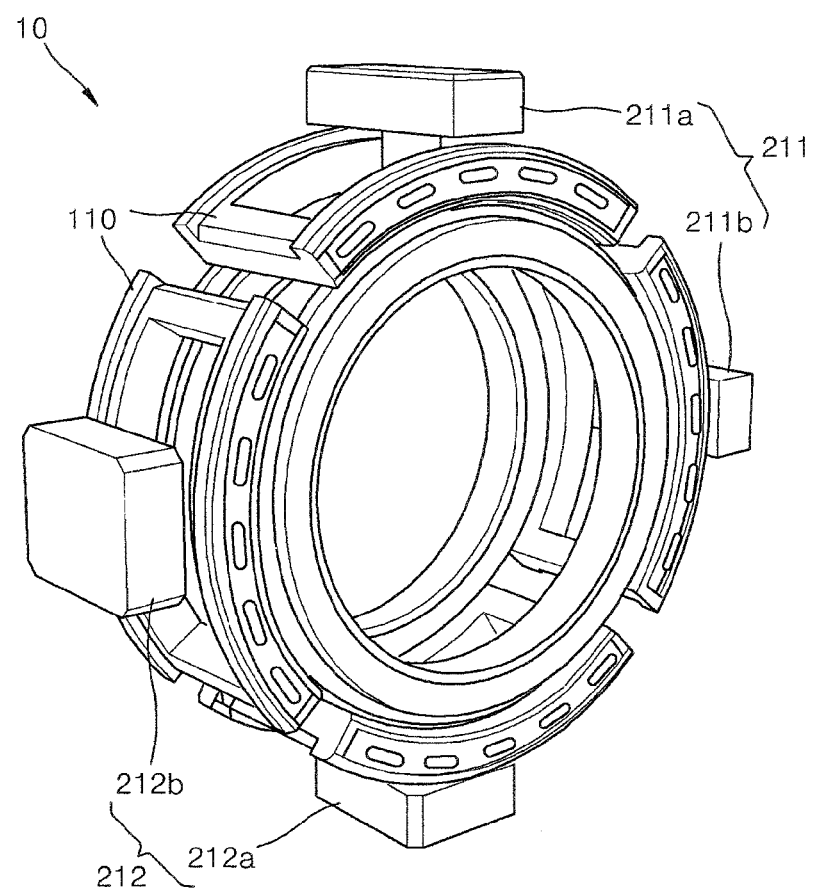
FIG. 5 is a view illustrating the inner structure of the brain/spinal imaging and microrobot driving unit of the microrobot driving system for the therapy of brain/spinal cord diseases in accordance with an embodiment of the present invention, established within a housing.

In the brain/spinal cord imaging and microrobot driving unit 10, the microrobot driving module 100 and the brain/spinal cord imaging module 200 may be arranged as shown in FIG. 5, but the present invention is not limited by the arrangement.

The microrobot driving module 100 may comprise an electromagnetic deriving coil system 110, a power supplier for supplying power to the coil system 110, and a control system for controlling the power supplied to the coil system 110. For use as a device for creating a desired electromagnetic field in a space under which a microrobot can be driven, the coil system 110 must be structured in consideration of factors responsible for the desired electromagnetic field, including coil shape, arrangement, and specification. As long as it generates such an electromagnetic field in a three-dimensional space so as to move a magnet or electric magnet in a specific direction, any coil system 110 may be used in the present invention (e.g., Anderst et al., Med, End. Phys. 31(1): 10-16, 2009; Jeong et al., Sensors and Actuators A, 157: 118-125, 2010; and Choi et al., Sensors and Actuators A 163: 410-417, 2010).

Figure 6:
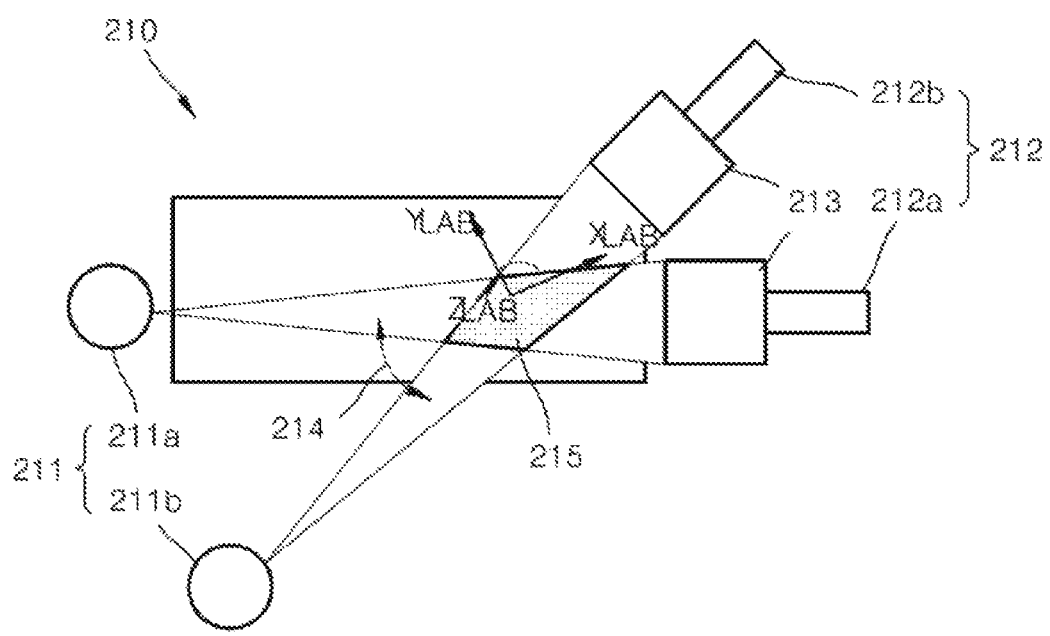
FIG. 6 is a view illustrating the principle of a brain/spinal cord imaging module of the microrobot driving system for the therapy of brain/spinal cord diseases in accordance with an embodiment of the present invention.

The brain/spinal cord imaging module 200 is adapted to produce pre-, intra-, and post-operative images of the space where the microrobot should move. In the present invention, pre-, intra-, and post-operative images are produced with the same X-ray angiographic device. To this end, a bi-plane angiographic device 210 is provided. The basic structure and principle of the X-ray angiographic device 210 is explained with reference to FIGS. 5 and 6. The bi-plane X-ray angiographic device 210 comprises two X-ray sources 211a and 211b and two image sensors 212a and 212b corresponding thereto, and may be optionally provided with an image intensifier 213 at a front end of the image sensor 212. The area of an angiographic zone 215 is determined according to an angle 214 between the two X-ray sources.

The working mechanism of the brain/spinal cord imaging module 200 is explained as follows. To begin with, a contrast medium is introduced into a zone to be imaged before the surgical operation. While the X-ray source 211 of the biplane X-ray angiographic device 210 is rotated at predetermined angles, two planar X-ray images are obtained at the angles. The planar images corresponding to the angles are combined and processed using a computer and computer-integrated image processing software to produce a three-dimensional pre-operative cerebrospinal image model. This is the X-ray CT (computer tomography) that allows the pre-operative diagnosis of a diseased lesion. During a surgical operation, a microrobot is introduced into a part of the brain/spinal cord and two respective plane images of the brain/spinal cord and the microrobot are obtained using the bi-plane X-ray angiographic device 210. Together with these two plane images, the pre-operative cerebrospinal image model is used to determine the position of the microrobot. Finally, post-operative cerebrospinal images are obtained, like pre-operative cerebrospinal images, using the bi-plane angiographic device 210, so that the effect of the surgical treatment can be determined.

Figure 7:
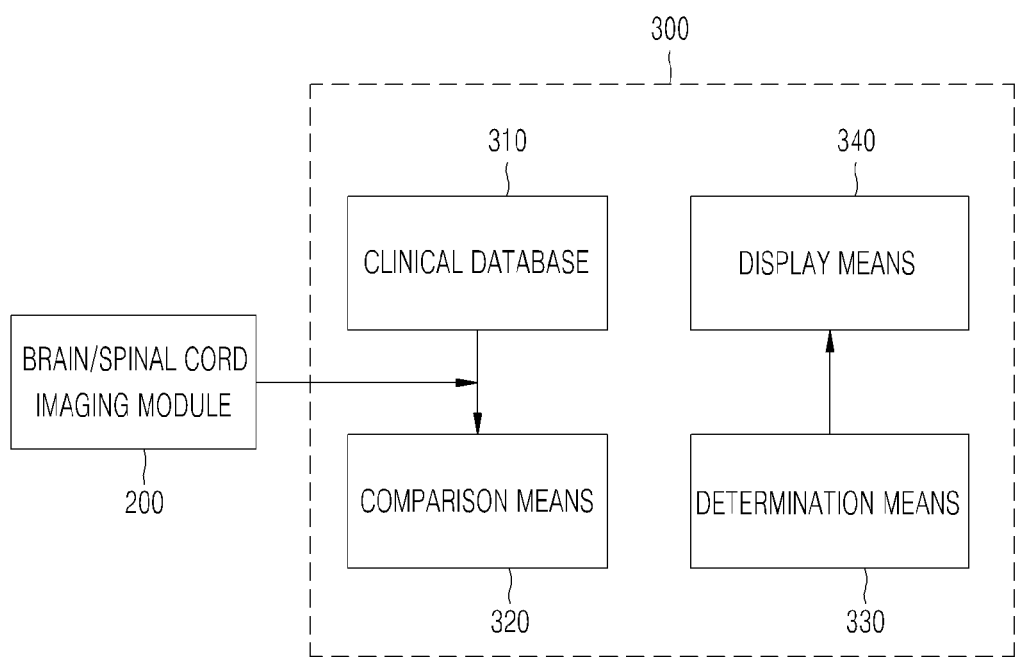
FIG. 7 is a schematic diagram illustrating the structure of a diagnosis module of the microrobot driving system for the therapy of brain/spinal cord diseases in accordance with an embodiment of the present invention.

The diagnosis module 300 is adapted to diagnose a lesion using the bi-plane X-ray angiographic device before or after the surgery. As shown in FIG. 7, the diagnosis module 300 comprises a clinical database 310, a comparison means 320 for comparing the clinical database with the image obtained through the bi-plane X-ray angiographic device 210, and a determination means 330 for determining the presence and severity of a disease. Optionally, when the diagnosis module 300 and the navigation module 400 are provided with hardware, the diagnosis module 300 may further comprise a display means for displaying the results determined by the determination means 330. Optionally, the clinical database may not be included within the diagnosis module 300, but supplied from an external source through the Internet or an intranet. An example of the diagnosis of a brain/spinal cord disease by the diagnosis module 300 is as follows. Hydrocephalus is a medical condition in which the cerebral ventricle swells as a result of abnormal accumulation of cerebrospinal fluid therein. On the basis of the clinical data accumulated in relation to the size of the ventricles, hydrocephalus can be diagnosed when the volume ratio of the ventricle to the whole brain exceeds a specific value. Thus, if a specific volume ratio of the whole brain/ventricle is calculated from the three-dimensional pre-operative cerebrospinal images obtained through the bi-plane X-ray angiographic device 210, hydrocephalus can be diagnosed by comparing the specific volume ratio with the clinical database 310, whether in-house or downloaded from an external source. Optionally, the diagnosis module 300 does not exclude the subjective decision of the doctor responsible for the operation of the system. Meanwhile, the clinical database 310, the comparison means 320, and the determination means 330 may be stored in the main memory device of the computer where the navigation module is installed, or may be separately stored in an auxiliary memory device for more effective operation. Further, the diagnosis module 300, the CT image processing software, and the navigation module 400 may be provided as separate software. If necessary, they may be provided as integrated software. Typically, the display means 340 is a monitor. It may be a dual monitor system in which two monitors are connected in series or in parallel, or a triple monitor system in which three monitors are connected in series or in parallel. The monitor may be a display device on which three-dimensional images can be displayed. In addition, the display means 340 may be exclusive to the determination module 300, or may be used both for displaying the pre- and/or intra-operative cerebrospinal images produced and processed by the brain/spinal cord imaging module 200 and for the navigation module 400. Optionally, under the condition that the diagnosis module 300 and the navigation module 400 of the microrobot driving system for the therapy of brain/spinal cord diseases in accordance with the present invention consist solely of software while the integrated control station 500 is separately provided, the display device of the integrated control station 500 may be used in lieu of the display means 340.

The navigation module 400 comprises a design means for planning a moving path of the microrobot with reference to the three-dimensional pre-operative cerebrospinal image model, and a microrobot indicating means for indicating the practical position of the microrobot using the three-dimensional pre-operative cerebrospinal image model and the intra-operative cerebrospinal images. In this context, the planned path through which the microrobot will be advanced to a target and the real path along which the microrobot moves are displayed simultaneously. Further, the navigation module may integrate a microrobot control unit (not shown) thereinto, which directs the microrobot to move along the planned path which has been overlaid on the microrobot indicating means. Optionally, the microrobot control unit may be a separate pointing device such as a joystick, a touchpad, a trackball, or a mouse.

The therapeutic microrobot 600, which constitutes, together with the microrobot driving system 1, the therapeutic microrobot system for brain/spinal cord diseases, functions to perform a medical treatment while moving in the brain/spinal cord, and comprises a driving unit in which a magnet is installed and a therapeutic means 620 for treating a lesion. That is, the microrobot 600 moves to a desired position in the presence of the electromagnetic field produced by the internal magnet and the driving module. In addition, the therapeutic means 620 can pierce an obstruction (the ependyma) and deliver a drug. Thus, the therapeutic means 620 may be a puncher or micro-scissors for microperforation or micro-dissection, a means for drug delivery, or a combination thereof.

Below, a description will be given of the therapeutic process in which the microrobot inserted into the body is driven to treat brain/spinal cord diseases by the microrobot driving system of the present invention with reference to the drawings.

Figure 8:
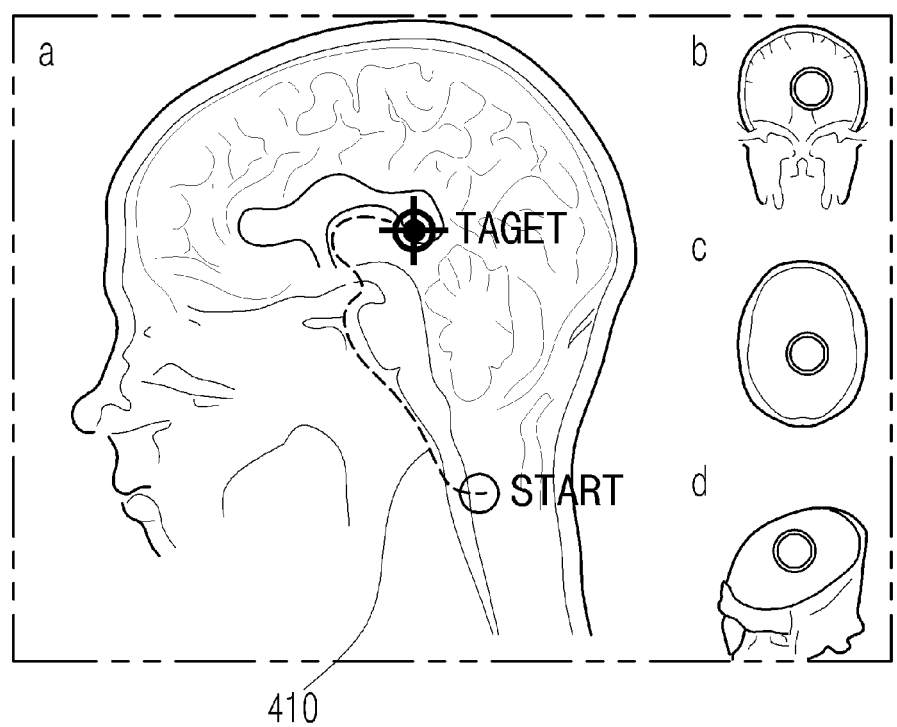
FIG. 8 shows images of a moving path of the microrobot, established in advance through a three-dimensional pre-operative cerebrospinal image model in accordance with one embodiment of the present invention:
   a: a sagittal plane cross-sectional view of the brain
   b: a coronal plane cross-sectional view of the brain
   c: a transverse plane cross-sectional view of the brain
   d: a three-dimensional cross-sectional view of the brain, constructed from the three views.

First, pre-operative three-dimensional cerebrospinal images are required for planning a moving path of the microrobot. FIG. 8 shows brain CT images of a patient as photographed by the bi-plane X-ray angiographic device 210. In the images, a moving path 410 which is established for an intrathecally injected microrobot to reach a target in a minimally invasive course is indicated as red dotted lines.

Figure 9:
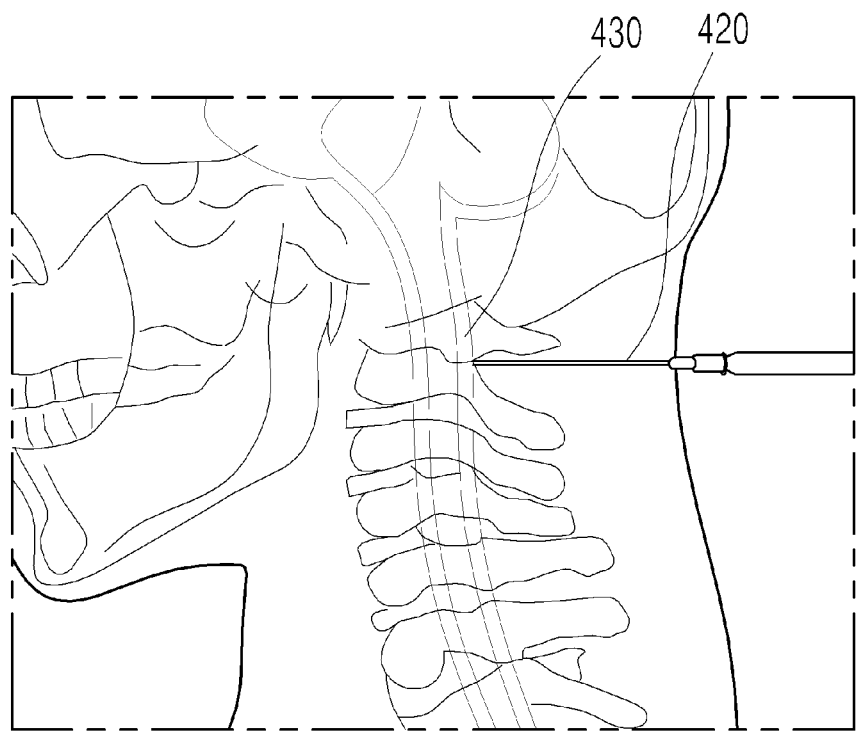
FIG. 9 is an image illustrating the injection of the microrobot into a thecal sac using a syringe.

Next, as shown in FIG. 9, the microrobot is intrathecally injected into a thecal sac 430 filled with cerebrospinal fluid using a syringe needle or a catheter. In this regard, the microrobot may be injected between the second and the third cervical vertebra (C2-C3), but the invention is not limited by this.

Figure 10:
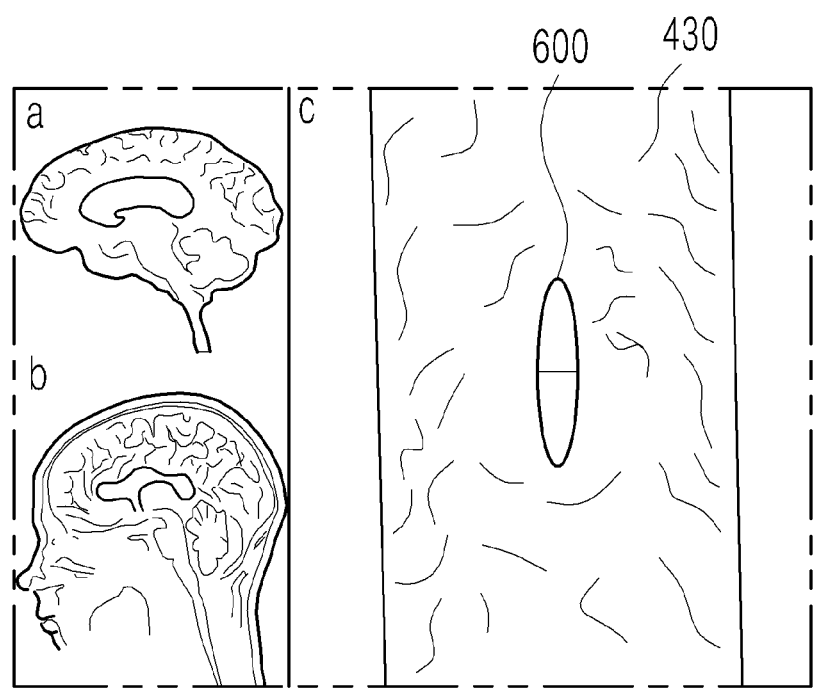
FIG. 10 is of images illustrating the locomotion of the microrobot within the brain using the microrobot driving system for the therapy of brain/spinal cord diseases in accordance with an embodiment of the present invention:
   a: a sagittal plane cross-sectional view showing an anatomical structure of the brain
   b: a sagittal plane cross-sectional view of the skull, photographed by cerebrospinal CT
   c: an imaginary picture showing the locomotion of the microrobot along the thecal sac.

The inserted microrobot 600, as shown in FIGS. 8 and 10, is directed to move through the established path along the thecal sac 430. Intraoperative images make it possible to monitor whether the real path of the microrobot is coincident with the planned moving path 410.

Figure 11:
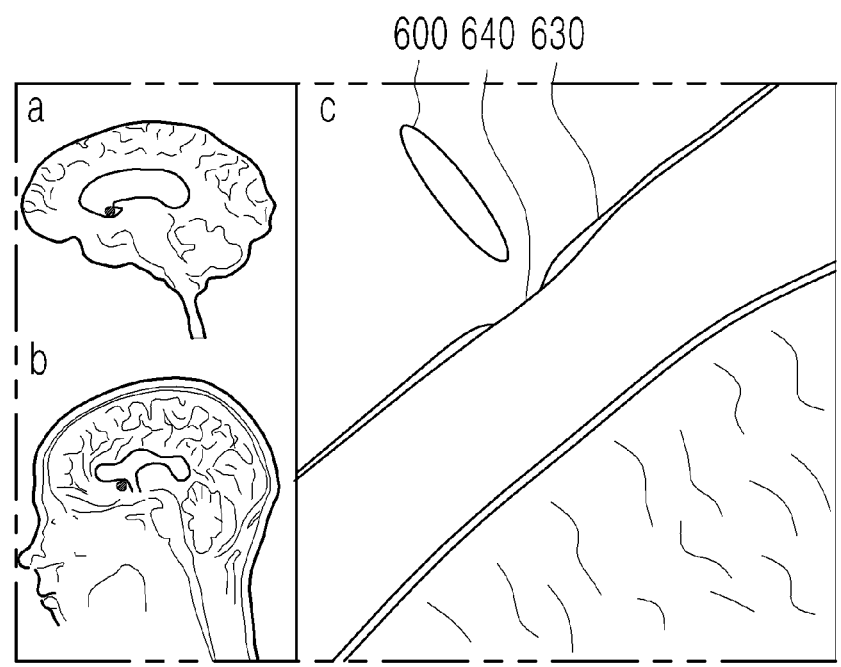
FIG. 11 shows images illustrating that the microrobot system for the therapy of brain/spinal cord diseases in accordance with an embodiment of the present invention perforates the ependyma:
   a: a sagittal plane cross-sectional view showing an anatomical structure of the brain
   b: a sagittal plane cross-sectional view of the skull, photographed by cerebrospinal CT
   c: an imaginary picture showing the microrobot that is punching the ependyma.

With reference to FIG. 11, a schematic view illustrating the process in which the microrobot driven by the microrobot driving system for the therapy of brain/spinal cord diseases acts to treat hydrocephalus is shown. After the microrobot 600 is allowed to approach a lesion by the microrobot driving module 100 and the driving unit 610 having a magnet therein (see FIG. 2), the therapeutic means 620 (see FIG. 2) loaded to the microrobot 600 perforates or dissects an ependyma 630 for the cerebrospinal fluid to flow down through a perforated or dissected hole 640. The microrobot may be equipped with the driving unit for driving the therapeutic means 620. In this case, the microrobot driving module 100 may be provided with a control unit for controlling the therapeutic means 620. The therapeutic means 620 may be a micro-puncher or micro-scissors.

Figure 12:
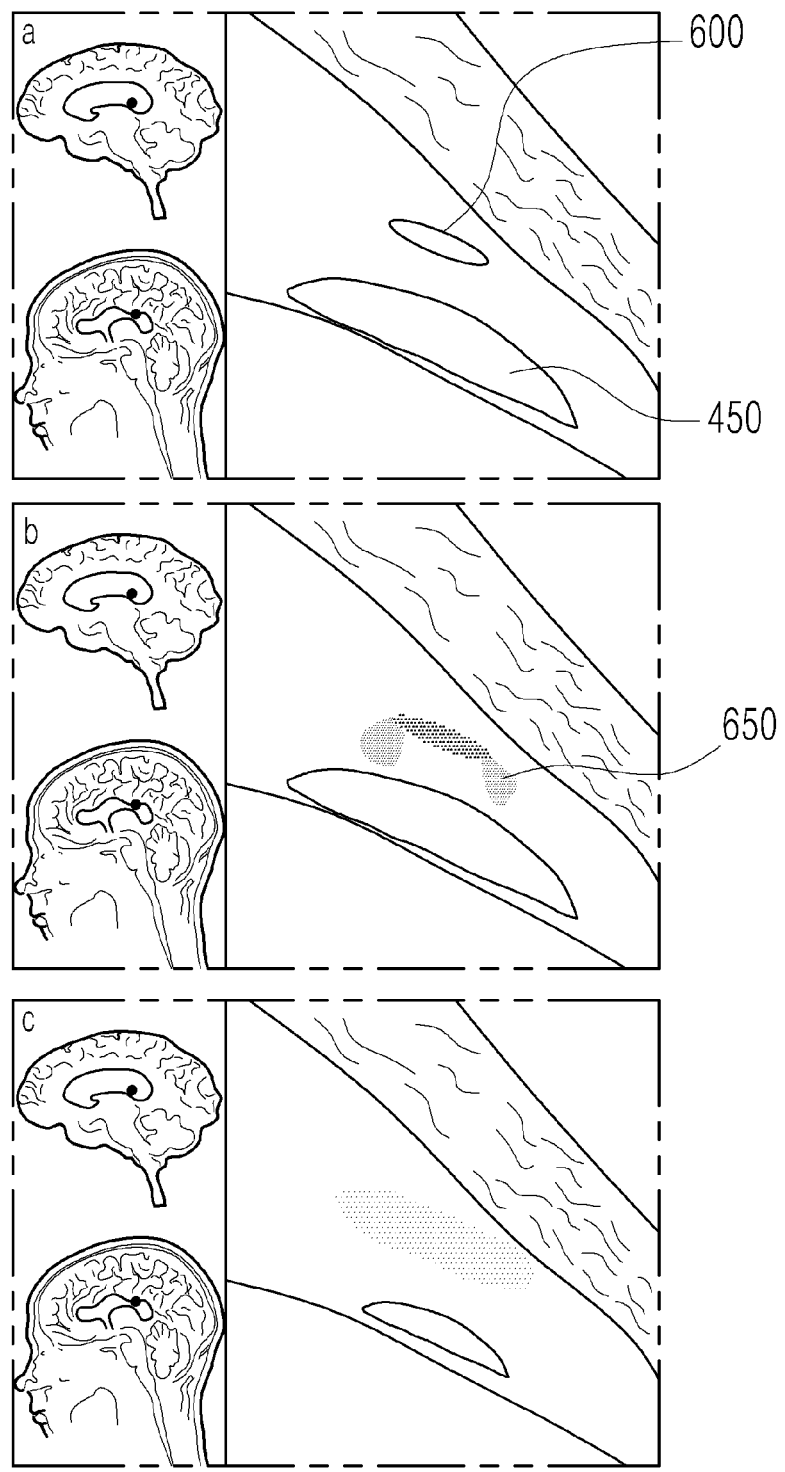
FIG. 12 shows images illustrating the delivery of a drug to a specific lesion by use of the microrobot system for the therapy of brain/spinal cord diseases in accordance with an embodiment of the present invention:
   a: an imaginary picture illustrating the arrival of the microrobot at a lesion;
   b: an imaginary picture illustrating the release of a drug from the microrobot into the lesion; and c: an imaginary picture illustrating the reduction of the lesion by the action of the drug.

With reference to FIG. 12, a schematic view illustrating a process in which the microrobot driven by the microrobot driving system for the therapy of brain/spinal cord diseases acts to treat a brain/spinal cord disease by delivering a drug specifically to a diseased region is shown, with the use of the therapeutic means 620 as a drug delivery means. When the microrobot is driven to reach a lesion 450 by the microrobot driving system, a drug 650 is released to treat the lesion. In this context, the therapeutic means of the microrobot 610 may comprise a reservoir for containing a drug, a valve for releasing the drug, and a driving unit for operating the valve, while the microrobot driving module 100 may be provided with a valve control unit for controlling the operation of the valve.

Figure 13:
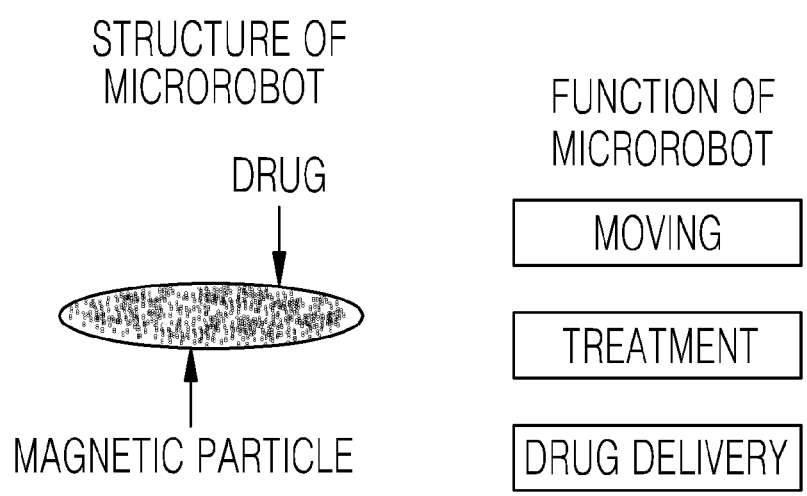
FIG. 13 is a schematic view illustrating the structure and function of the microrobot system for the therapy of brain/spinal cord diseases in accordance with an embodiment of the present invention.

In accordance with one embodiment of the present invention, the microrobot for the therapy of brain/spinal cord diseases, as shown in FIG. 13, may be structured so that magnetic particles are dispersed in a drug. In this regard, the magnetic particle-dispersed drug may be loaded into a capsule made of a biocompatible material which can be degraded in a lesion-specific manner, thus releasing the drug specifically to the lesion. The magnetic particles released together with the drug can be recovered using the microrobot driving system of the present invention.

Optionally, the microrobot for the therapy of brain/spinal cord diseases according to the present invention may be structured such that microspheres encapsulating a drug and micromagnetic particles are dispersed in a biocompatible matrix. In this case, the microspheres may be coated with a biocompatible material. Examples of the biocompatible matrix or material include collagen, cellulose, cellulose acetate, polyvinyl alcohol, polyethylene glycol, HEMA, PLA, PLGA, PGA, hyaluronic acid, alginic acid, polylysine, polydimethylsiloxane, and chitosan, but are not limited thereto.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A microrobot system for therapy of a brain/spinal cord disease, comprising:
    a microrobot comprising a driving unit having a magnet therein, and a therapeutic means or drug delivery means for treating a disease lesion;
    a microrobot driving module performing and controlling various motions of the microrobot by generating an electromagnetic force through an electromagnetic coil system;
    an imaging module imaging a thecal sac filled with cerebrospinal fluid, a ventricle, and the microrobot, the imaging module extracting and producing three-dimensional images using a bi-plane X-ray angiographic device;
    a diagnosis module diagnosing the brain/spinal cord disease, based on a pre-operative image produced by the imaging module; and
    a navigation module planning a moving path for the microrobot and monitoring the microrobot, the navigation module including
        a design means planning the moving path of the microrobot using the pre-operative image produced by the imaging module, and
        a microrobot position indicating means identifying a position of the microrobot by comparing an intra-operative image with the pre-operative image produced by the imaging module.

2. The microrobot system of claim 1, wherein the therapeutic means of the microrobot is a puncher or micro-scissors.

3. The microrobot system of claim 1, wherein the microrobot driving module comprises the electromagnetic coil system, a power supply for supplying an electric power to the coil system, and an electric power controlling system.

4. The microrobot system of claim 1, wherein the diagnosis module comprises:
    a comparison means for comparing the pre-operative image produced by the imaging module with clinical data;
    a determination means for determining a disease, based on a comparison result obtained by the comparison means; and
    a display means for displaying a determination result obtained by the determination means.

5. A method for treating a brain/spinal cord disease using a microrobot, comprising:
    extracting and processing a three-dimensional pre-operative cerebrospinal image using a bi-plane X-ray angiographic device;
    planning a moving path of the microrobot from the three-dimensional pre-operative cerebrospinal image using a navigation module;
    introducing the microrobot into a thecal sac of a patient, where the microrobot is equipped with a driving unit having a magnet therein, and a therapeutic means or a drug delivery means;
    detecting positions of a ventricle, the thecal sac, and the microrobot with the bi-plane X-ray angiographic device and the navigation module by photographing intra-operative cerebrospinal images;
    moving the microrobot along the planned moving path using a microrobot driving module equipped with an electromagnetic coil system;
    allowing the microrobot to reach a lesion, followed by performing a medical treatment for a lesion using the therapeutic means or the drug delivery means; and
    extracting the microrobot counter to the moving path under control of the microrobot driving module to exclude the microrobot from the body.

6. The method of claim 5, where the navigation module comprises:
    a design means for planning a moving path of the microbot with reference to the three-dimensional pre-operative cerebrospinal image extracted and processed by the bi-plane X-ray angiographic device; and
    a microrobot indicating means for indicating a position of the microrobot using three-dimensional pre- and intra-operative images.

7. The method of claim 5, wherein the microrobot driving module comprises the electromagnetic coil system, a power supply for supplying an electric power to the coil system, and an electric power controlling system.

8. The method of claim 5, wherein the microrobot is introduced into the thecal sac using a syringe needle or a catheter.

9. The method of claim 5, wherein the therapeutic means is a puncher for perforating an obstruction or micro-scissors for dissecting an obstruction, said obstruction including an ependyma.

* * * * *